United States Patent [19]

Malewicz

[11] Patent Number: 5,759,165
[45] Date of Patent: Jun. 2, 1998

[54] FOREARM SUPINATION RANGE-OF-MOTION ORTHOSIS

[75] Inventor: Andrzej M. Malewicz, Minneapolis, Minn.

[73] Assignee: Empi, Inc., St. Paul, Minn.

[21] Appl. No.: 597,667

[22] Filed: Feb. 7, 1996

Related U.S. Application Data

[63] Continuation-in-part of Ser. No. 388,482, Feb. 14, 1995, Pat. No. 5,520,625, which is a continuation-in-part of Ser. No. 205,837, Mar. 4, 1994, Pat. No. 5,437,619, which is a continuation-in-part of Ser. No. 85,758, Jun. 30, 1993, Pat. No. 5,399,154.

[51] Int. Cl.$^6$ .................................................. A61F 5/00
[52] U.S. Cl. .................................................. 602/21; 602/16
[58] Field of Search ......................... 623/18, 20, 39; 482/127, 136; 602/5, 16, 20, 21, 23, 26, 27; 473/464, 615, 518, 474, 458, 412, 207, 22, 59, 63

[56] References Cited

U.S. PATENT DOCUMENTS

| | | |
|---|---|---|
| 1,847,823 | 3/1932 | Dresser. |
| 2,395,768 | 2/1946 | Svoboda. |
| 3,086,521 | 4/1963 | Desai et al.. |
| 4,180,870 | 1/1980 | Radulovic et al.. |
| 4,252,111 | 2/1981 | Chao et al.. |
| 4,280,490 | 7/1981 | Santy ......................... 602/16 |
| 4,397,308 | 8/1983 | Hepburn. |
| 4,433,679 | 2/1984 | Mauldin et al.. |
| 4,456,002 | 6/1984 | Barber et al.. |
| 4,485,808 | 12/1984 | Hepburn. |
| 4,489,718 | 12/1984 | Martin. |
| 4,493,316 | 1/1985 | Reed et al.. |
| 4,508,111 | 4/1985 | Hepburn. |
| 4,520,804 | 6/1985 | DiGeorge. |
| 4,538,600 | 9/1985 | Hepburn. |
| 4,565,190 | 1/1986 | Pirmantgen et al.. |
| 4,633,867 | 1/1987 | Kausek et al.. |
| 4,657,000 | 4/1987 | Hepburn. |
| 4,726,361 | 2/1988 | Farley. |
| 4,738,252 | 4/1988 | Friddle et al.. |
| 4,817,588 | 4/1989 | Bledsoe. |
| 4,844,057 | 7/1989 | Hoy. |
| 4,862,878 | 9/1989 | Davison et al.. |
| 5,203,766 | 4/1993 | Carter et al. ......................... 602/21 |
| 5,407,420 | 4/1995 | Bastyr et al. ......................... 602/20 X |

FOREIGN PATENT DOCUMENTS

1426-580-A 2/1987 U.S.S.R..

*Primary Examiner*—Richard J. Apley
*Assistant Examiner*—Kim M. Lee
*Attorney, Agent, or Firm*—Kinney & Lange, P.A.

[57] ABSTRACT

A range-of-motion orthosis for applying torque across a forearm of a patient is disclosed. The orthosis includes a support hook for supporting a hand of the patient. First pivot means pivotally connects the support hook to a forearm bracket. The forearm bracket includes first and second portions interconnected at an angle of between 80° and 100°. Second pivot means pivotally connects the forearm bracket to an upper arm bracket such that the first portion of the forearm bracket is capable of rotation about an axis intersecting the second pivot means. A first upper arm hook is connected to the upper arm bracket for supporting an upper arm of the patient. Torque applying means interconnects the forearm bracket and the upper arm bracket and applies torque between the forearm bracket and the upper arm bracket, thereby rotating the first portion of the forearm bracket about the axis intersecting the second pivot means.

22 Claims, 7 Drawing Sheets

FOREARM SUPINATION RANGE-OF-MOTION ORTHOSIS

REFERENCE TO RELATED APPLICATIONS

This application is a continuation-in-part of commonly assigned U.S. patent application Ser. No. 08/388,482, filed Feb. 14, 1995, now U.S. Pat. No. 5,520,625 entitled "RANGE-OF-MOTION WRIST SPLINT", which is a continuation-in-part of Ser. No. 205,837, filed Mar. 4, 1994, now commonly assigned U.S. Pat. No. 5,437,619, granted Aug. 1, 1995, entitled "RANGE-OF-MOTION SPLINT WITH ECCENTRIC SPRING", which is a continuation-in-part of Ser. No. 085,758, filed Jun. 30, 1993, now commonly assigned U.S. Pat. No. 5,399,154, granted Mar. 21, 1995, entitled "CONSTANT TORQUE RANGE-OF-MOTION SPLINT".

BACKGROUND OF THE INVENTION

The present invention relates to orthosis assemblies, and more particular to dynamic orthoses or braces for applying torque across a limb undergoing rehabilitative therapy.

Injury or surgery to human joints, such as wrists and elbows, often result in flexion or extension contractures. These debilitating conditions prevent the patient from fully flexing (in the case of an extension contracture) or extending (in the case of a flexion contracture) the injured joint. Range-of-motion (ROM) orthoses are dynamic devices commonly used during physical rehabilitative therapy to increase the range-of-motion over which the patient can flex or extend the joint. Orthoses of this type are known, and disclosed, for example, in U.S. Pat. No. 5,399,154 entitled "CONSTANT TORQUE RANGE-OF-MOTION SPLINT" and in U.S. Pat. No. 5,437,619 entitled "RANGE-OF-MOTION SPLINT WITH ECCENTRIC SPRING".

Commercially available ROM orthoses typically include spring loaded brace or bracket sections or applying torque to the insured joint in opposition to the contracture. This force tends to gradually increase the working range or angle of joint motion. Springs, however, are passive devices and exert decreasing amounts of force as they retract. Most ROM orthoses, therefore, require continual adjustment to maintain a constant amount of applied torque as the patient's range of joint motion increases during therapy. These torque adjustment procedures are time consuming and inconvenient.

In addition, with respect to an injury to a patient's wrist or elbow, the forearm of the patient is often immobilized for a significant length of time. Thus, in addition to the wrist and elbow suffering from flexion or extension contractures, the connecting tissue surrounding the forearm have become debilitated.

The forearm is made up of two separate bones: the ulna bone and the radius bone. The ulna bone is a long bone positioned at the inner side of the forearm, while the radius bone is a shorter bone positioned at the outer side of the forearm. The two bones interconnect at their upper extremities near the elbow joint and at their lower extremities near the wrist joint.

When a patient's forearm has been immobilized for a significant length of time, the connecting tissue surrounding the ulna and radius bones are debilitated. Therefore, the ability to twist the forearm toward the body, thereby turning the palm of the hand downward (pronation) and the ability to twist the forearm away from the body, thereby turning the palm of the hand upward (supination) is both difficult and painful. It is necessary to provide low level stretching of the connecting tissue surrounding the ulna and radius bones of the forearm so that pronation and supination is again possible.

Therefore, it is evident that there is a continuing need for an improved ROM orthosis. In particular, there is a need for a ROM orthosis capable of applying relatively constant torque over the entire working range-of-motion of the forearm to rehabilitate the connecting tissue surrounding the ulna and radius bones of the forearm with respect to pronation and supination. The amount of torque applied by the orthosis should be adjustable to suit the needs of different patients. The orthosis should also provide for the natural motion of the forearm.

SUMMARY OF THE INVENTION

The present invention is a range-of-motion orthosis for providing torque across a forearm of a patient undergoing rehabilitative therapy. The range-of-motion orthosis is designed so that it provides for the natural motion of the forearm.

The range of motion orthosis comprises a support hook for supporting a hand of a patient and a forearm bracket consisting of a first portion and a second portion. The second portion of the forearm bracket is connected to the first portion of the forearm bracket at an angle of between 80° and 100°. First pivot means pivotally connects the support hook to the forearm bracket. Second pivot means pivotally connects the forearm bracket to an upper arm bracket such that the first portion of the forearm bracket is capable of rotation about an axis intersecting the second pivot means. A first upper arm hook is connected to the upper arm bracket for supporting an upper arm of the patient. Torque applying means positioned near the second pivot means applies torque between the forearm bracket and the upper arm bracket, thereby rotating the first portion of the forearm bracket about the axis intersecting the second pivot means.

In a preferred embodiment, the forearm bracket further comprises a first forearm telescoping bracket for connection to the first pivot means and a second forearm telescoping bracket for connection to the upper arm bracket. A forearm securing pin secures the first forearm telescoping bracket to the second forearm, telescoping bracket. Similarly, the upper arm bracket further comprises a first upper arm telescoping bracket for connection to the forearm bracket and a second upper arm telescoping bracket for connection to the first upper arm telescoping bracket. An upper arm securing pin secures the first upper arm telescoping bracket to the second upper arm telescoping bracket.

DETAILED DESCRIPTION OF THE PREFERRED EMBODIMENTS

Figure 1:
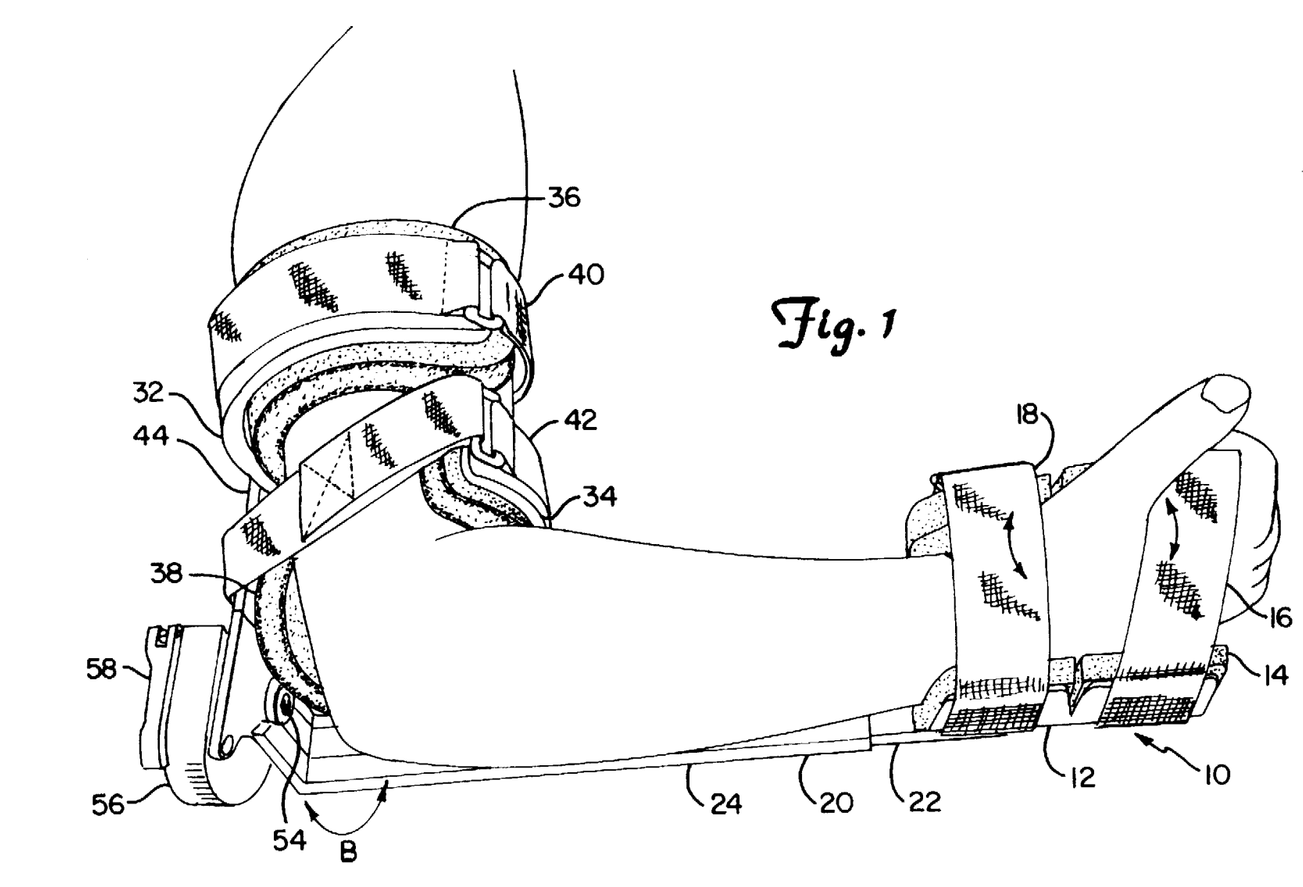
FIG. 1 is a first perspective view of the present invention shown attached to an arm of a patient.
Figure 2:
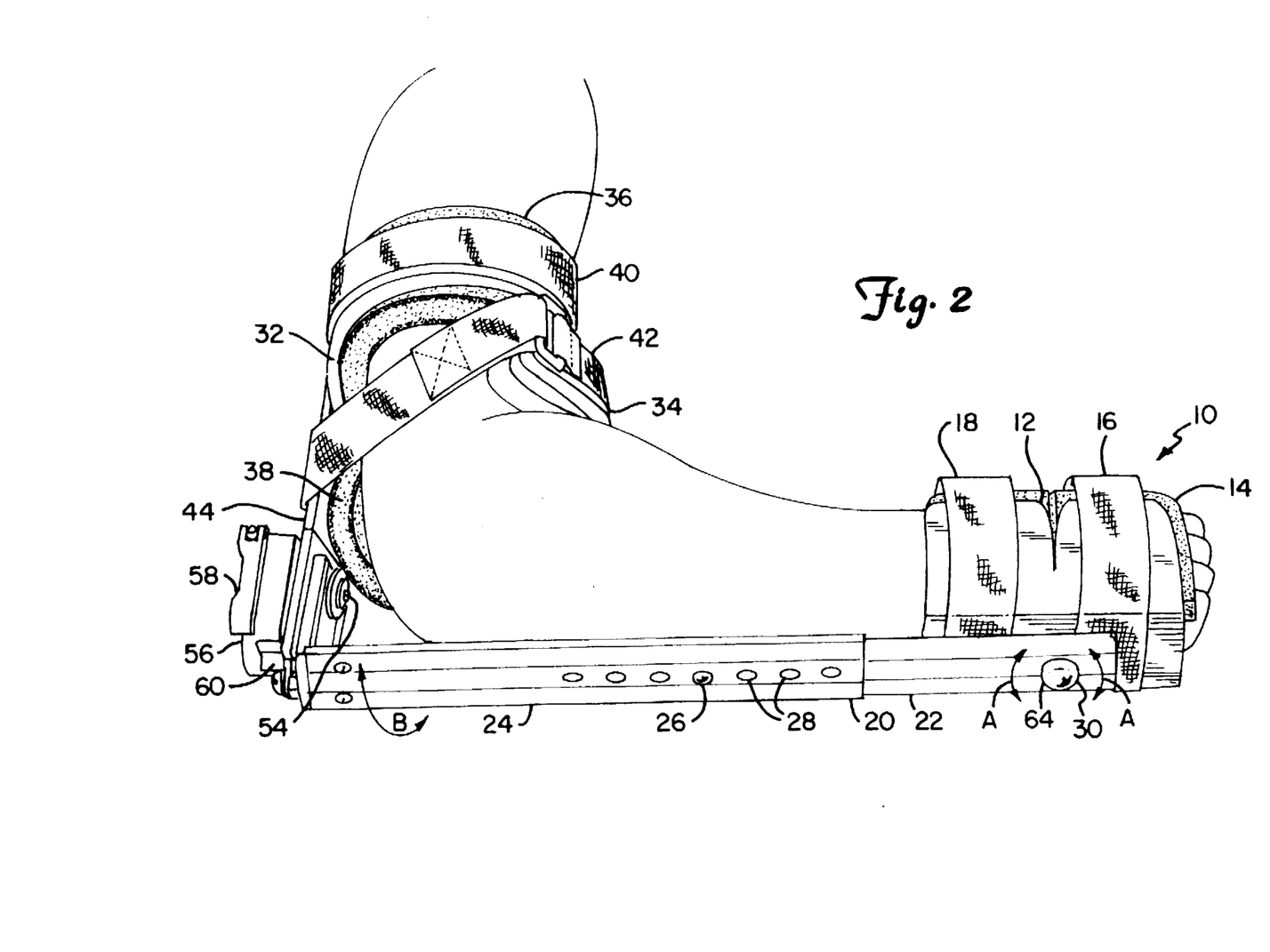
FIG. 2 is a second perspective view of the present invention shown attached to the arm of the patient.
Figure 3:
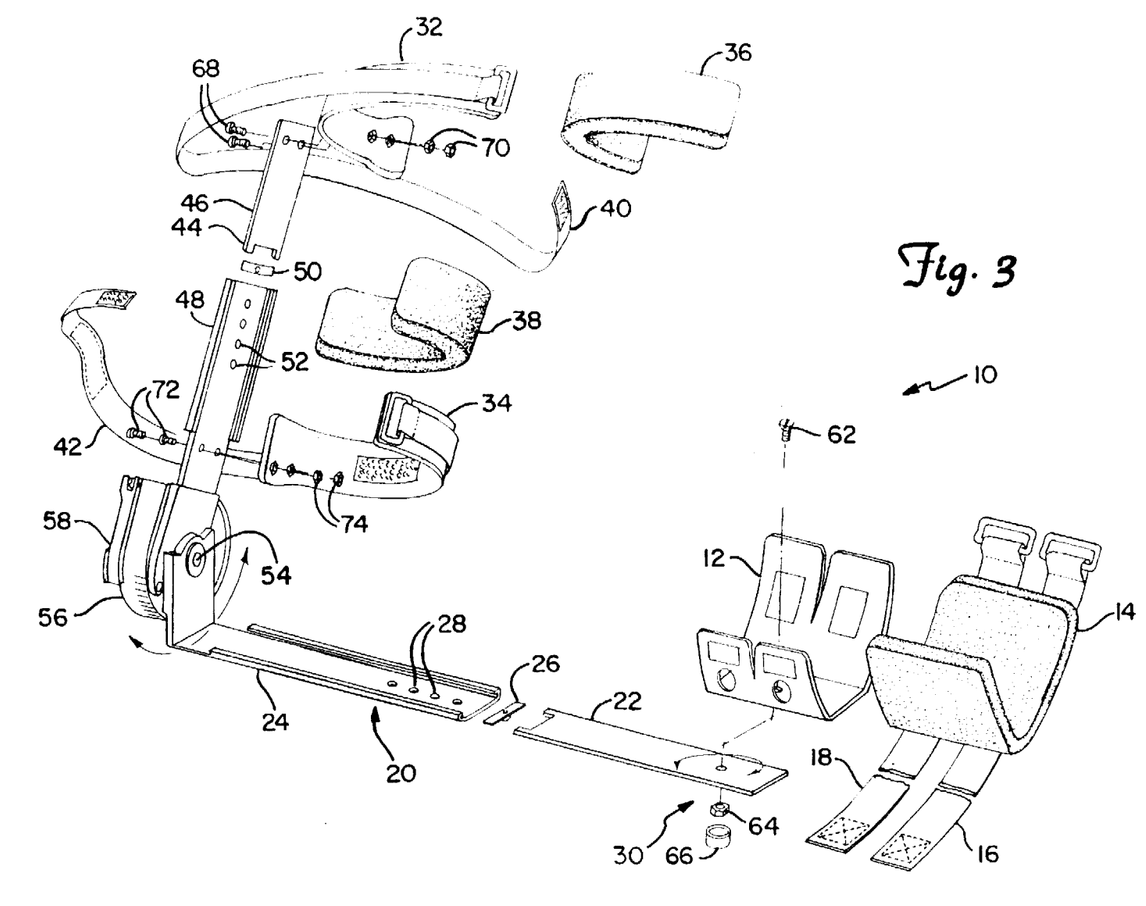
FIG. 3 is an exploded view of the present invention.

The present invention relates to range-of-motion (ROM) orthosis 10 shown in FIGS. 1-3 for applying torque across a limb undergoing rehabilitive therapy. FIG. 1 is a perspective view of ROM orthosis 10 attached to a forearm of a patient. In FIG. 1, ROM orthosis 10 is shown in a first position. FIG. 2 is also a perspective view of ROM orthosis 10 attached to a forearm of a patient. FIG. 2 shows ROM orthosis 10 in a second position. FIG. 3 is a exploded view of ROM orthosis 10.

As shown in FIGS. 1-3, ROM orthosis 10 includes support hook 12, support hook pad 14, first support hook securing straps 16, second support hook securing strap 18, forearm bracket 20 comprising first forearm telescoping bracket 22 and second forearm telescoping bracket 24, pin 26, holes 28, pivotal connector 30, first upper arm hook 32 second upper arm hook 34, first upper arm hook pad 36, second upper arm hook pad 38, first upper arm hook securing strap 40, second upper arm hook securing strap 42, upper arm bracket 44 comprising first upper arm telescoping bracket 46 and second upper arm telescoping bracket 48, pin 50, holes 52, pivotal connector 54, housing 56 having handle 58 and lock 60.

As shown in FIGS. 1-3 support hook 12 is connected to first forearm telescoping bracket 22 Of forearm bracket 20 via screw 62 and nut 64 (shown in FIG. 3). Support hook 12 supports the hand of the patient. Cap 66 covers screw 62 and nut 64 in order to prevent any rough edges from being exposed. In one preferred embodiment, screw 62 and nut 64 are replaced by a rivet. Support hook pad 14 can be either one pad or a series of pads. Pad 14 can be formed to the inside of support hook 12 and secured to support hook 12 by any number of methods, including the use of VELCRO material.

First and second support hook securing straps 16 and 18 can be secured to the outer surface of support hook 12 via various materials, such as Velcro material. First and second support hook securing straps 16 and 18 are used to secure the wrist and hand area of the patient to ROM orthosis 10. As shown in FIG. 1 first and second support hook securing straps 16 and 18 can be positioned about the thumb of the patient. This type of design provides for both proper support and comfort.

As shown in FIGS. 2 and 3, support hook 12, with its accompanying support hook pad 1 is connected to first forearm telescoping bracket 29 via pivotal connector 30. Support hook 12 is capable of rotation with respect to first forearm telescoping bracket 22 by way of pivotal connector 30 comprising screw 69 and nut 64 positioned beneath cap 66. The rotation of support hook 12 with respect to forearm bracket 20 is shown in FIG. 2 by arrows A. The amount of tension supplied at this pivot point can be adjusted by adjusting screw 62 and nut 64. Rotation of support hook 12 about pivotal connector 30 corresponding to screw 62 and nut 64 allows the patient to position his hand in comfortable configurations, thereby providing low level stretching of connecting tissue surrounding the ulna and radius bones of the forearm.

First forearm telescoping bracket 22 is interconnected with second forearm telescoping bracket 24 via pin 26 and holes 28. As shown in FIG. 3 pin 26 can be fastened to first forearm telescoping bracket 22. Thus, it is possible to adjust the length of forearm bracket 20 by placing pin 26 in any of various holes 28. The adjustable nature of forearm bracket 20 provides that ROM orthosis 10 can be secured to any number of patients having various forearm lengths. This feature provides additional comfort for the patient.

First upper arm hook 32 is secured to first upper arm telescoping bracket 46 via screws 68 and nuts 70. In one preferred embodiment, screws 68 and nuts 70 can be replaced by rivets. Likewise, second upper arm hook 34 is connected to second upper arm telescoping bracket 48 via screws 72 and nuts 74. Once again in one preferred embodiment, screws 72 and nuts 74 can be replaced by rivets. First and second upper arm hook pads 36 and 38 can be attached to first and second upper arm hooks 32 and 34 via a variety of means, such as the use of VELCRO material. First and second upper arm hook pads 36 and 38 provide comfort for the patient. First and second upper arm hook securing straps 40 and 42 are secured to first and second upper arm hooks 32 and 34 via any number of means, such as through the use of VELCRO material. First and second upper arm hook securing straps 40 and 42 secure ROM orthosis 10 to the upper arm of the patient and provide the proper stability points such that ROM orthosis operates properly. First and second upper arm telescoping brackets 46 and 48 are interconnected via pin 50 and holes 52 in a manner similar to the connection of first and second forearm telescoping brackets 22 and 24. The adjustable nature of upper arm bracket 44 provides that ROM orthosis 10 can be secured to any number of patients having various upper arm lengths. This feature provides additional comfort for the patient.

As shown in FIGS. 1-3, second forearm telescoping bracket 24 includes first and second portions connected at an angle of between 80 and 100 degrees, preferably 90 degrees. This configuration allows first forearm telescoping bracket 22 and the first portion of second forearm telescoping bracket 24 to rotate about an axis which intersects pivotal connector 54. This rotation is shown in FIGS. I and 2 by arrow B. Pivotal connector 54 connects forearm bracket 20 to upper arm bracket 44. The approximate center of the forearm of a patient can lie in the same axis as the axis which intersects pivotal connector 54. Once ROM orthosis 10 is properly positioned on a patient, ROM orthosis 10 can provide low level stretching of connecting tissue surrounding the ulna and radius bones of the forearm of the patient. These tissues often become debilitated when a patient has had his arm immobilized for a significant length of time, i.e. a broken wrist or forearm.

Figure 4:
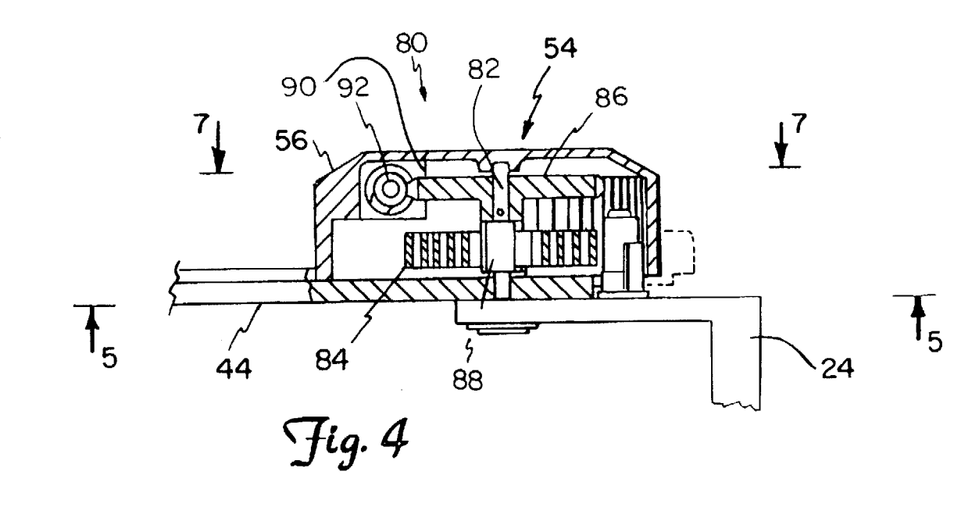
FIG. 4 is a sectional view of the pivotal connector of the present invention as shown from line 4—4 of FIG. 1.

FIG. 4 is a sectional view of pivotal connector 54 enclosed within housing 56 as shown from line 4—4 of FIG. 1. As shown in FIG. 4, housing 56 encloses drive assembly 80 which further includes pin 82, spiral spring 84, gear 86, gear shaft 88, recess 90 of housing 56 and adjustment worm 92.

As shown in FIG. 4, spring 84 and gear 86 are positioned about pivot pin 82, which also serves to permit forearm bracket 24 to rotate with respect to upper arm bracket 44. More specifically, spiral spring 84 is positioned about shaft 88 which encompasses pivot pin 82. An inner end of spiral spring 84 is mounted to upper arm bracket 44 and an outer end of spiral spring 84 is mounted to forearm bracket 24.

Figure 5:
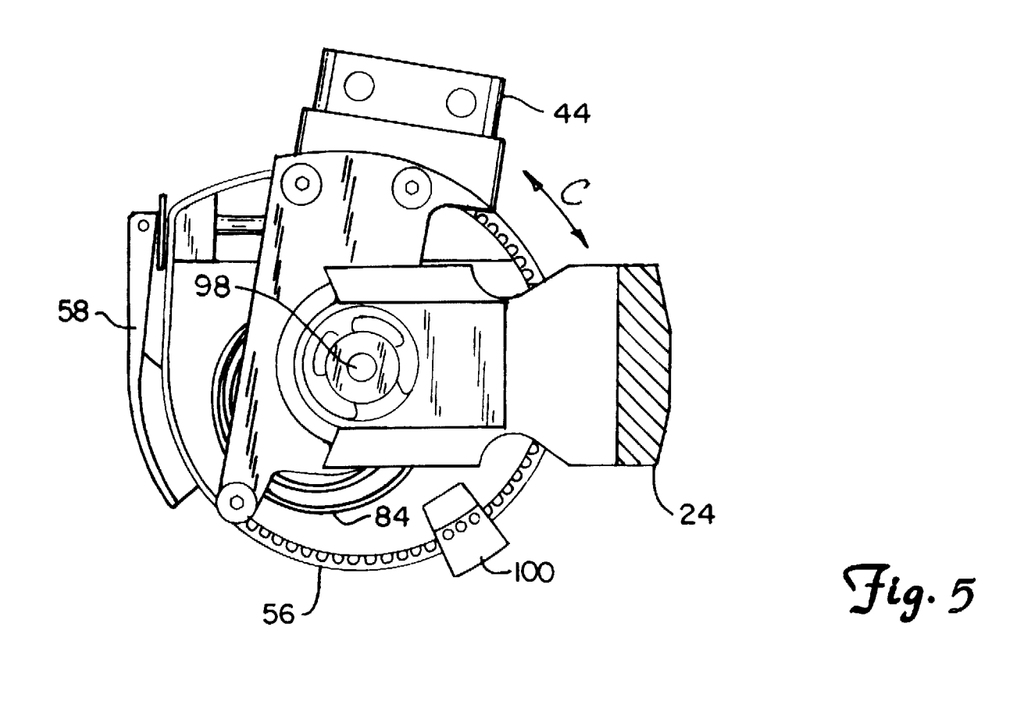
FIG. 5 is a detailed view of the drive assembly as shown from line 5—5 of FIG. 4, illustrating the pivot assembly in a first position.
Figure 6:
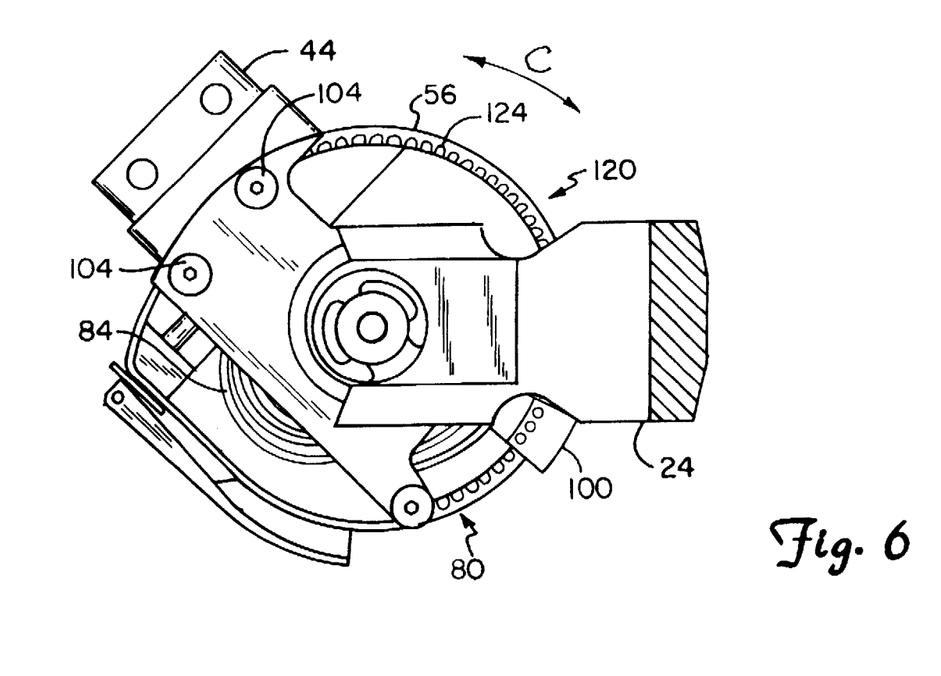
FIG. 6 is a detailed view of the drive assembly as shown from line 5—5 of FIG. 4, illustrating the pivot assembly in a second position.

FIGS. 5 and 6 are detailed views of the drive assembly as shown from line 5—5 of FIG. 4, illustrating the pivot assembly in a first and second position, respectively. As shown in FIG. 5, forearm bracket 24 is free to rotate with respect to upper arm bracket 44 to increase angle C. However, as shown in FIG. 6, adjustment range-of-motion stop mechanism 100 prevents forearm bracket 24 from rotating with respect to upper arm bracket 44 to increase angle C. Adjustable range-of-motion stop mechanism is used to prevent a range-of-motion which may injure the limb of the patient. In certain instances, a physician or clinician may wish to limit the range-of-motion which a patient can utilize.

Figure 7:
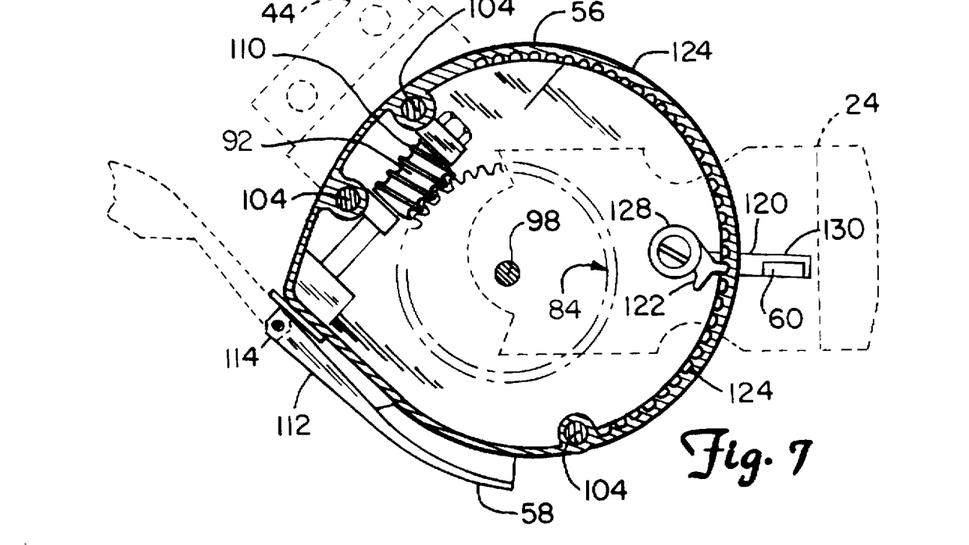
FIG. 7 is a detailed view of the drive assembly as shown from line 7—7 of FIG. 4, illustrating the torque adjustment mechanism.
Figure 8:
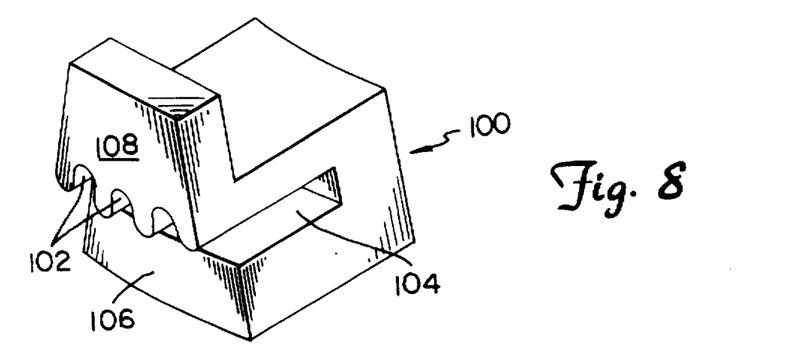
FIG. 8 is a pictoral view of an adjustable range-of-motion stop mechanism.
Figure 8A:
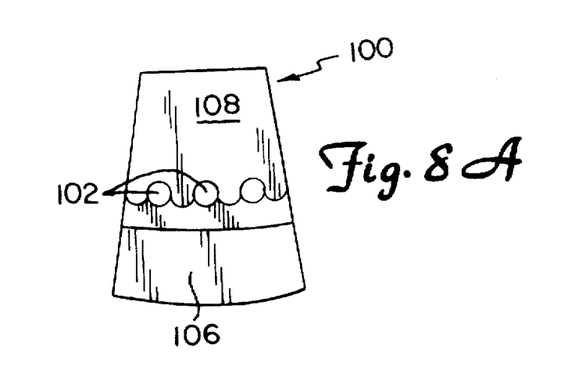
FIG. 8A is a top view of the adjustable range-of-motion stop mechanism.

FIGS. 8 and 8A are a pictoral view and a top view of the range-of-motion stop mechanism used in the present invention, respectively. Adjustable ROM stop mechanism 100 can be made of molded plastic, metal or any other suitable material. Adjustable ROM stop mechanism 100 includes series of grooves 102, slot 104, back 106 and handle 108. Series of grooves 102 interacts with rack 124 positioned on the inner surface of housing 56 (shown in FIGS. 5-7) to hold adjustable ROM stop mechanism 100 in place. Back 106 and slot 104 have a slight arc to them such that they precisely conform to the outer surface of housing 56.

In use, adjustable ROM stop mechanism 100 can be placed at any one of a plurality of positions on housing 56. Forearm bracket 24 can rotate with respect to upper arm bracket 44 until forearm bracket 24 comes in contact with adjustable ROM stop mechanism 100. At this point, forearm bracket 24 can no longer rotate with respect to upper arm bracket 44.

Adjustable ROM stop mechanism 140 enables a clinician to control the extent of rotational motion between upper arm bracket 44 and forearm bracket 24. This is necessary to prevent damage to the connecting tissue surrounding the ulna and radius bones of the forearm of the patient due to overextension.

As shown in FIGS. 4 and 7, a torque adjustment mechanism is shown which includes adjustment worm 92 having end 110, crank 112 having handle 58, and pivot 114.

As shown in FIGS. 4 and 7, adjustment worm 92 is mounted within recess 90 of housing 56 for engagement with gear 86. End 110 of adjustment worm 92 extends through housing 56 and is connected to crank 112 by pivot pin 114. Crank 112 is configured for pivotal movement about a retracted position adjacent housing 56 (shown in solid lines), and an extended position (shown in broken lines). When in the extended position, handle 58 of crank 112 can be actuated to rotate adjustment worm 92 which is rotatably connected to upper arm bracket 44, thereby rotating gear 86 rotatably connected to upper arm bracket 44 to wind and unwind spiral spring 84 in order to increase and decrease the amount of torque applied across upper arm bracket 44 and forearm bracket 24 by spring 84. Gear 86, adjustment worm 92 and crank 112 thereby function as a torque adjustment mechanism.

FIGS. 4 and 7 show locking mechanism 120 which can releasably lock upper arm bracket 44 and forearm bracket 24 with respect to one another. Locking mechanism 120, connected to forearm bracket 24, includes pawl 122, rack 124, lock lever 60 and base member 128 having handle 130. Pawl 122 is actuated by lock lever 60 which includes base member 128 and handle 130. Base member 128 is mounted to pawl 122 and extends outwardly from housing 56. Handle 130 extends from base member 128 and is positioned generally adjacent to the exterior of housing 56. Handle 130 is actuated to drive pawl 122 between a position disengaged from rack 124, and a position engaged with rack 124. When pawl 122 is in the disengaged position, upper arm bracket 44 and forearm bracket 24 can freely rotate with respect to one another. Conversely, when pawl 122 is in the engaged position, pawl 122 is biased into engagement with rack 124 such that upper arm bracket 44 and forearm bracket 24 are incapable of rotation.

Locking mechanism 120, connected to forearm bracket 24, enables upper arm bracket 44 and forearm bracket 24 to be conveniently and rigidly locked with respect to one another at any desired position within the range-of-motion of orthosis 10. In one embodiment, the teeth forming rack 124 are symmetrical or bi-directional. Housing 56 can therefore be used on range-of-motion orthosis 10 configured for both supination and pronation contractures of an elbow joint.

Although the present invention has been described with reference to preferred embodiments, workers skilled in the art will recognize that changes may be made in form and detail without departing from the spirit and scope of the invention.

What is claimed is:

1. A range-of-motion orthosis adapted to apply torque to a forearm of a patient, the orthosis comprising:

a support hook adapted to support a hand of the patient;

a forearm bracket;

connection means for connecting the forearm bracket to the support hook;

an upper arm bracket;

a first upper arm hook connected to the upper arm bracket;

a second upper arm hook connected to the upper arm bracket;

pivot means pivotally connected to the upper arm bracket and the forearm bracket such that the forearm bracket rotates about a longitudinal axis of the forearm; and torque applying means connected to the forearm bracket and the upper arm bracket for applying torque to the forearm bracket such that the forearm bracket rotates about a longitudinal axis of the forearm.

2. The range-of-motion orthosis of claim 1 wherein the connection means further comprises:

support hook pivot means for pivotally connecting the forearm bracket to the support hook such that the support hook can rotate with respect to the forearm bracket about the support hook pivot means.

3. The range-of-motion orthosis of claim 1 wherein the forearm bracket further comprises:

a first forearm telescoping bracket for connection to the first pivot means;

a second forearm telescoping bracket having a first portion and a second portion, wherein the first portion is connected to the second portion at an angle of between 80° and 100°;

a forearm securing pin for securing the first forearm telescoping bracket to the second forearm telescoping bracket;

wherein the first portion of the second forearm telescoping bracket interconnects with the upper arm bracket via the second pivot means, and wherein the second portion of the second forearm telescoping bracket interconnects with the first forearm telescoping bracket; and wherein the first forearm telescoping bracket and the second portion of the second forearm telescoping bracket are capable of rotation about an axis of the second pivot means.

4. The range-of-motion orthosis of claim 1 wherein the upper arm bracket further comprises:
   a first upper arm telescoping bracket for connection to the forearm bracket; and
   a second upper arm telescoping bracket for connection to the first telescoping bracket; and
   an upper arm securing pin for securing the first upper arm telescoping bracket to the second upper arm telescoping bracket.

5. The range-of-motion orthosis of claim 1 and further comprising:
   a support hook securing means connected to the support hook adapted to secure the support hook to a hand of the patient;
   a first upper arm hook securing means connected to the first upper arm hook adapted to secure the first upper arm hook to an upper arm of the patient; and
   a second upper arm hook securing means connected to the second upper arm hook adapted to secure the second upper arm hook to the upper arm of the patient.

6. The range-of-motion orthosis of claim 5 and further comprising:
   a support hook pad connected to the support hook;
   a first upper arm hook pad connected to the first upper arm hook; and
   a second upper arm hook pad connected to the second upper arm hook.

7. The range-of-motion orthosis of claim 1 wherein the torque applying means further comprises:
   a spiral spring having an inner end and an outer end for applying torque between the forearm bracket and the upper arm bracket, the inner end mounted to the upper arm bracket and the outer end mounted to the forearm bracket.

8. The range-of-motion orthosis of claim 7 and further comprising:
   a torque adjustment mechanism for adjusting the torque applied by the spiral spring between the forearm bracket and the upper arm bracket.

9. The range-of-motion orthosis of claim 8 wherein the torque adjustment mechanism further comprises:
   a gear rotatably connected to the upper arm bracket such that the inner end of the spring is connected to the gear; and
   an adjustment worm rotatably connected to the upper arm bracket and engaged with the gear for rotating the gear to adjust the tension of the spiral spring.

10. The range-of-motion orthosis of claim 8 and further comprising:
    a cover connected to the upper arm bracket for enclosing the spiral spring and the torque adjustment mechanism; and
    a handle connected to the adjustment worm and capable of movement between a retracted position adjacent the cover and an expanded position, such that the handle can rotate the adjustment worm when in the extended position.

11. The range-of-motion orthosis of claim 10 and further comprising:
    a locking mechanism connected to the forearm bracket for releasably engaging the cover and locking the angular position of the forearm bracket with respect to the upper arm bracket.

12. The range-of-motion orthosis of claim 11 wherein the locking mechanism further comprises:

a rack positioned on an inner surface of the cover;
    a pawl pivotally connected to the forearm bracket for releasable engagement with the rack; and
    a lever connected to the pawl and extending from the cover for actuating the pawl.

13. A range-of-motion orthosis for applying torque to a forearm of a patient, the orthosis comprising:
    a support hook adapted to support a hand of the patient;
    a forearm bracket comprising:
       a first portion; and
       a second portion connected to the first portion at an angle of between 80° and 100°;
    first pivot means for pivotally connecting the support hook to the first portion of the forearm bracket;
    an upper arm bracket;
    second pivot means pivotally connected to the second portion of the forearm bracket and the upper arm bracket such that the first portion of the forearm bracket rotates about a longitudinal axis of the forearm;
    a first upper arm hook connected to the upper arm bracket for supporting an upper arm of the patient; and
    torque applying means connected to the forearm bracket and the upper arm bracket for applying torque to the forearm bracket such that the forearm bracket rotates about a longitudinal axis of the forearm.

14. The range-of-motion orthosis of claim 13 wherein the first portion of the forearm bracket further comprises:
    a first forearm telescoping bracket for connection to the first pivot means;
    a second forearm telescoping bracket for connection to the second portion of the forearm bracket; and
    a forearm securing pin for securing the first forearm telescoping bracket to the second forearm telescoping bracket.

15. The range-of-motion orthosis of claim 13 wherein the upper arm bracket further comprises:
    a first upper arm telescoping bracket for connection to the forearm bracket;
    a second upper arm telescoping bracket for connection to the first upper arm telescoping bracket; and
    an upper arm securing pin for securing the first upper arm telescoping bracket to the second upper arm telescoping bracket.

16. The range-of-motion orthosis of claim 13 and further comprising:
    a support hook securing means connected to the support hook for securing the support hook to a hand of the patient;
    a first upper arm hook securing means connected to the first upper arm hook for securing the first upper arm hook to an upper arm of the patient;
    a second upper arm hook connected to the upper arm bracket for supporting the upper arm of the patient;
    a second upper arm hook securing means connected to the second upper arm hook for securing the second upper arm hook to the upper arm of the patient;
    a support hook pad connected to the support hook;
    a first upper arm hook pad connected to the first upper arm hook; and
    a second upper arm hook pad connected to the second upper arm hook.

17. The range-of-motion orthosis of claim 13 wherein the torque applying means further comprises:

a spiral spring having an inner end and an outer end for applying torque between the forearm bracket and the upper arm bracket, the inner end mounted to the upper arm bracket and the outer end mounted to the forearm bracket.

18. The range-of-motion orthosis of claim 17 and further comprising:

a torque adjustment mechanism for adjusting the torque applied by the spiral spring between the forearm bracket and the upper arm bracket.

19. The range-of-motion orthosis of claim 18 wherein the torque adjustment mechanism further comprises:

a gear rotatably connected to the upper arm bracket such that the inner end of the spring is connected to the gear; and an adjustment worm rotatably connected to the upper arm bracket and engaged with the gear for rotating the gear to adjust the tension of the spiral spring.

20. The range-of-motion orthosis of claim 19 and further comprising:

a cover connected to the upper arm bracket for enclosing the spiral spring and the torque adjustment mechanism; and a handle connected to the adjustment worm and capable of movement between a retracted position adjacent the cover and an expanded position, such that the handle can rotate the adjustment worm when in the extended position.

21. The range-of-motion orthosis of claim 20 and further comprising:

a locking mechanism connected to the forearm bracket for releasably engaging the cover and locking the angular position of the forearm bracket with respect to the upper arm bracket.

22. The range-of-motion orthosis of claim 21 wherein the locking mechanism further comprises:

a rack positioned on an inner surface of the cover;

a pawl pivotally connected to the forearm bracket for releasable engagement with the rack; and a lever connected to the pawl and extending from the cover for actuating the pawl.

* * * * *